(12) United States Patent
Lim et al.

(10) Patent No.: US 10,932,738 B2
(45) Date of Patent: Mar. 2, 2021

(54) X-RAY IMAGING DEVICE WITH SUBJECT ALIGNMENT DEVICE

(71) Applicants: VATECH Co., Ltd., Gyeonggi-do (KR); VATECH EWOO Holdings Co., Ltd., Gyeonggi-do (KR)

(72) Inventors: Hyung Keun Lim, Gyeonggi-do (KR); Jin Pyo Chun, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 73 days.

(21) Appl. No.: 15/117,231

(22) PCT Filed: Feb. 9, 2015

(86) PCT No.: PCT/KR2015/001277
§ 371 (c)(1),
(2) Date: Aug. 8, 2016

(87) PCT Pub. No.: WO2015/119467
PCT Pub. Date: Aug. 13, 2015

(65) Prior Publication Data
US 2016/0338662 A1    Nov. 24, 2016

(30) Foreign Application Priority Data
Feb. 7, 2014 (KR) .................. 10-2014-0014029

(51) Int. Cl.
*A61B 6/00* (2006.01)
*A61B 6/04* (2006.01)
(Continued)

(52) U.S. Cl.
CPC ............ *A61B 6/465* (2013.01); *A61B 6/0492* (2013.01); *A61B 6/461* (2013.01); *A61B 6/462* (2013.01);
(Continued)

(58) Field of Classification Search
CPC .......... A61B 6/00; A61B 6/04; A61B 6/0492; A61B 6/08; A61B 6/14; A61B 6/46; A61B 6/462; A61B 6/465; A61B 6/467; A61B 6/469; A61B 6/54; A61B 6/542; A61B 6/544; A61B 6/545; A61B 6/58; A61B 6/582; A61B 6/587; A61B 6/589;
(Continued)

(56) References Cited

U.S. PATENT DOCUMENTS 4,293,771 A * 10/1981 Lescrenier ............... A61B 6/08
356/138
7,632,015 B2 * 12/2009 Stayman ................ A61B 6/032
378/163

(Continued)

FOREIGN PATENT DOCUMENTS

KR   10-2012-0036997 A   4/2012
WO   2013/014488 A1      1/2013
WO   2013/188617 A1      12/2013

*Primary Examiner* — Anastasia Midkiff
(74) *Attorney, Agent, or Firm* — IP Legal Services, LLC

(57) ABSTRACT

The present invention relates to an imaging device for an X-ray image and, particularly, to an imaging device for an X-ray image which enables a posture of a patient to be checked and corrected in real time when an X-ray image of a specific part of a patient's body is to be imaged.

6 Claims, 2 Drawing Sheets

(51) Int. Cl.
*A61B 6/08* (2006.01)
*A61B 6/03* (2006.01)
*A61B 6/14* (2006.01)

(52) U.S. Cl.
CPC .............. *A61B 6/467* (2013.01); *A61B 6/469* (2013.01); *A61B 6/582* (2013.01); *A61B 6/587* (2013.01); *A61B 6/589* (2013.01); *A61B 6/032* (2013.01); *A61B 6/04* (2013.01); *A61B 6/08* (2013.01); *A61B 6/14* (2013.01); *A61B 6/4435* (2013.01)

(58) Field of Classification Search
CPC ........... G01N 2223/00; G01N 2223/30; G01N 2223/32; G01N 2223/321; G01N 2223/323; H01J 37/02; H01J 37/20; H01J 37/22; H01J 37/30; H01J 37/3002; H01J 37/3005; H01J 37/302; H01J 2237/024; H01J 2237/15; H01J 2237/1501; H01J 2237/20; H01J 2237/202; H01J 2237/20292; H01J 2237/248; H01J 2237/2482

See application file for complete search history.

(56) References Cited

U.S. PATENT DOCUMENTS

| | | | |
|---|---|---|---|
| 2008/0181359 A1 | 7/2008 | Stayman et al. | |
| 2011/0026671 A1 | 2/2011 | Shi et al. | |
| 2012/0051520 A1* | 3/2012 | Hoernig | A61B 6/107 |
| | | | 378/98.5 |
| 2012/0163544 A1* | 6/2012 | Mizrahi | A61B 5/0422 |
| | | | 378/98.2 |
| 2013/0094748 A1 | 4/2013 | Shi et al. | |
| 2014/0139215 A1 | 5/2014 | Gregerson et al. | |
| 2014/0147803 A1 | 5/2014 | Lecuyer et al. | |
| 2014/0368545 A1* | 12/2014 | Ban | A61B 6/03 |
| | | | 345/634 |

\* cited by examiner

X-RAY IMAGING DEVICE WITH SUBJECT ALIGNMENT DEVICE

CROSS REFERENCE TO RELATED APPLICATIONS

This application is a National Stage Patent Application of PCT International Patent Application No. PCT/KR2015/001277 (filed on Feb. 9, 2015) under 35 U.S.C. § 371, which claims priority to Korean Patent Application No. 10-2014-0014029 (filed on Feb. 7, 2014), the teachings of which are incorporated herein in their entireties by reference.

TECHNICAL FIELD

The present disclosure relates to a radiography machine, and more particularly, to a radiography machine which can check and correct the posture of a patient in real time when a specific body part of the patient is intended to be radiographed.

BACKGROUND ART

In general, during radiography, it is very important to perform radiography after checking whether the posture of a patient or a specific part of the patient is correctly positioned in an imaging area, in order to obtain a radiograph at a correct position. At this time, the posture of the patient may include various motions. For example, the patient may move the body or keep the balance, and the position of the patient in the imaging area may be corrected.

According to a conventional method for measuring the posture of a patient, laser beam is irradiated on a specific part of the patient such that an operator determines whether the posture of the patient is correct. In particular, when a radiograph of the oral cavity and teeth of the patient is intended to be obtained, laser beam is irradiated on the face of the patient, and the operator corrects the posture or position of the patient based on the irradiated laser beam.

When laser beam is irradiated to measure and correct the posture of a patient, the laser beam irradiated on the face of the patient may be directly irradiated on the eyeballs of the patient, because each patient has a different face contour or head size.

Furthermore, a radiography machine for radiographing the oral cavity and teeth of a patient may block the view of a patient or the view of an operator in some cases. In this case, the operator must correct the posture of the patient while watching a face image of the patient, which is taken through a camera or the like. Thus, it is difficult for the operator to exactly correct the posture of the patient, thereby increasing the psychological anxiety of the patient.

Moreover, since the operator must handle the detail settings of the radiography machine while correcting the posture of the patient, the moving line of the operator may be increased more than necessary.

When the posture of the patient does not reach a reference point of laser beam, an accurate radiograph cannot be obtained. Thus, re-radiographing frequently occurs.

DISCLOSURE OF INVENTION

Technical Problem

Various embodiments are directed to a radiography machine which is safe for a patent and enables an operator to easily check and correct the posture of the patient when the patient is intended to be radiographed.

The technical problems are not limited thereto, and other technical problems which are not described will be clearly understood by those skilled in the art based on the following descriptions.

Technical Solution

A radiography machine may include: an alignment unit configured to provide alignment criteria for radiographing a subject; and a subject check unit disposed to overlap at least one surface of the subject to be aligned according to the alignment criteria.

The subject check unit may include a transparent plate or transparent display.

The alignment unit may include: a radiography unit including a radiation source and a detector; and a housing unit housing the radiation source and the detector, and defining an alignment area for the subject between the radiation source and the detector, and the subject check unit may be installed in the housing unit to surround a part of the alignment area.

The subject check unit may include a transparent touch panel.

The subject check unit may further include a preference setting interface configured to control detail settings of the radiography unit according to a user command inputted by a touching interface.

The subject check unit may have a guide line being displayed to overlap a specific part of the subject.

The guide line may be displayed by laser beam.

Advantageous Effects

The present invention has the following excellent effects.

In the radiography machine according to the embodiment of the present invention, as the transparent subject check unit is disposed, an operator can observe a subject with the eye through the subject check unit, and the view of the patient can be opened to reduce the psychological anxiety of the patient.

Furthermore, the guide line may be displayed on the transparent subject check unit, instead of a body part of the patient as the subject, which makes it possible to prevent the patient from being directly exposed to laser beam for forming the guide line.

Moreover, when the subject check unit is implemented with a touch panel, the operator can not only identify the subject, but also control the preference settings of radiography.

NUMERALS

Figure 1:
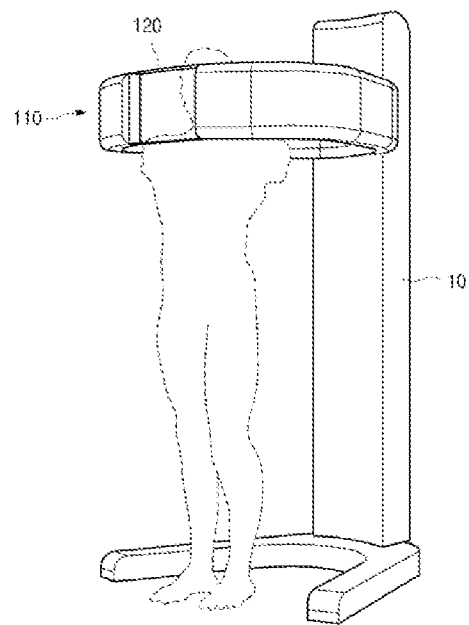
FIG. 1 is a diagram illustrating a radiography machine according to an embodiment of the present invention.

110: Alignment unit
111: Radiography unit

112: Housing unit
120: Subject check unit
121: Guide line

MODE FOR CARRYING OUT INVENTION

The terms used in this specification were selected as general terms which are widely used. However, the terms may include terms which were arbitrarily selected by the present applicant in specific cases. In this case, the meanings of the terms should be not simply understood through the terms, but understood in consideration of meanings described or used in the detailed descriptions of the present invention.

Hereafter, exemplary embodiments of the present invention will be described in detail with reference to the accompanying drawings.

However, the present invention is not limited to the exemplary embodiments, but may be embodied into another form. Throughout the specification, like reference numerals represent the same elements.

Figure 2:
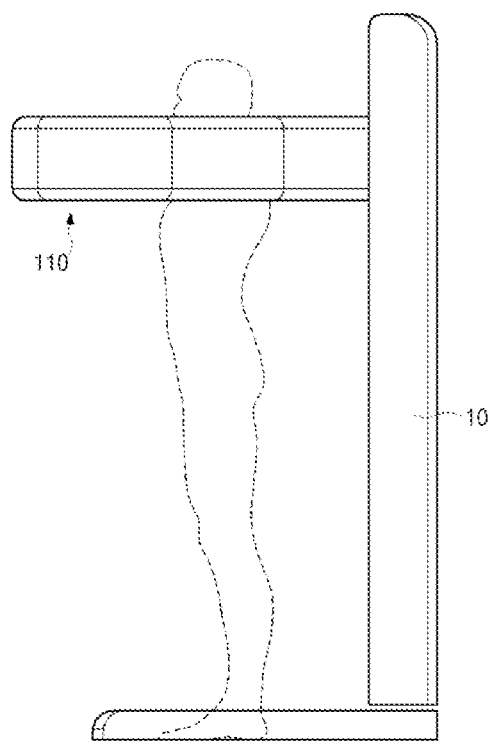
FIG. 2 is a side view illustrating the radiography machine according to the embodiment of the present invention.
Figure 3:
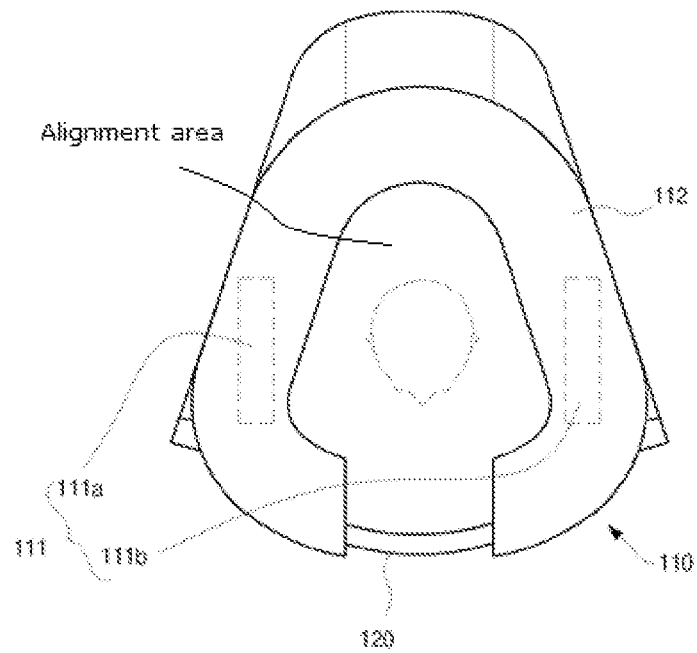
FIG. 3 is a plan view illustrating the radiography machine according to the embodiment of the present invention.
Figure 4:
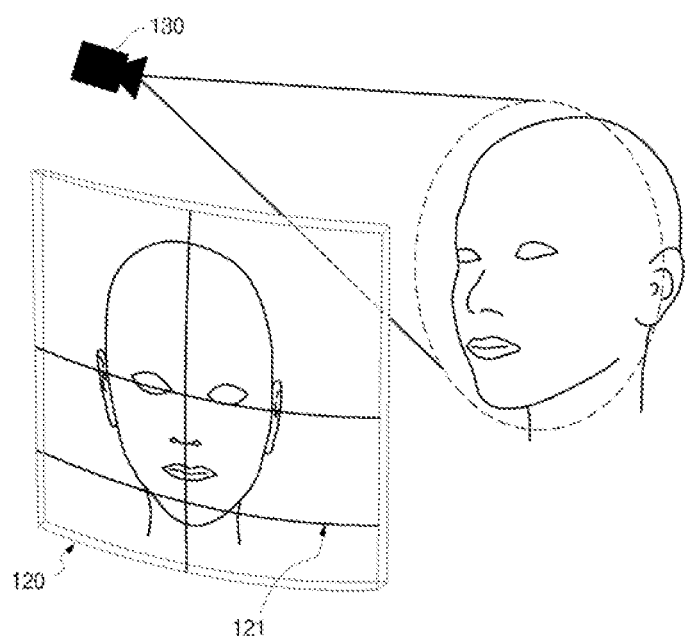
FIG. 4 is a diagram illustrating a subject check unit according to the embodiment of the present invention.

FIG. 1 is a diagram illustrating a radiography machine according to an embodiment of the present invention, FIG. 2 is a side view illustrating the radiography machine according to the embodiment of the present invention, FIG. 3 is a plan view illustrating the radiography machine according to the embodiment of the present invention, and FIG. 4 is a diagram illustrating a subject check unit according to the embodiment of the present invention.

Referring to FIGS. 1 to 4, the radiography machine according to the embodiment of the present invention enables a user to check the posture of a patient in real time when radiographing a specific part of the patient for medical use, and includes an alignment unit 110 and a subject check unit.

The alignment unit 110 may be integrated with a radiography unit which emits radiation toward a patient so as to obtain a radiograph, or disposed separately from the radiography unit such that the patient can be positioned while taking a posture.

The alignment unit 110 may be used for checking and correcting the posture of a patient in a variety of medical fields. In particular, the alignment unit 110 may be used in a dental clinic such that an operator radiographs the oral cavity or teeth of the patient while checking and correcting the posture of the patient.

The alignment unit 110 provides an alignment area and alignment criteria for a subject who is intended to be radiographed. Thus, when radiation is emitted toward a patient positioned in the alignment area, the posture or specific part of the patient can be correctly positioned in a radiograph.

The alignment area indicates a predetermined region where a subject is to be positioned for radiography, and the alignment criteria indicate a variety of means for setting a specific part of the subject, for example, the oral cavity or teeth of the subject at a correct position in the radiograph.

The alignment unit 110 may provide an internal space where the subject can stand or sit, and may be fixed to a support 10 or wall such that the entire body part of the patient or only a specific part of the patient can be positioned the space. For another example, the alignment unit 110 may include a bite block which is held in the mouth of the patient such that a patient can be accurately positioned at the alignment criteria or a head rest or ear rod for fixing the head of the patient.

The alignment unit 110 includes a radiography unit 111 and a housing unit 112, and the radiography unit 111 may be embedded in the housing unit 112.

The radiography unit 111 may emit radiation toward a subject, and include a radiation source 111a for emitting radiation and a detector 111b for detecting the radiation emitted from the radiation source.

The housing unit 112 serves to house the radiation source 111a and the detector 111b. The radiation source 111a and the detector 111b may be embedded in the housing unit 112 in a state where the radiation source 111a and the detector 111b face each other. If necessary, the housing unit 112 may define a rotation area in which the radiation source 111a and the detector 111b are rotated in a predetermined angle range while facing each other, in order to perform CT scanning.

The housing unit 112 may be formed in a donut shape, a cylindrical shape or polygonal shape, and have an internal space in which a patient or a specific part of the patient can be positioned. At least a part of the housing unit 112 may be opened to install the subject check unit 120 which will be described below.

The housing unit 112 may be vertically moved in a state where the housing unit 112 is fixed to the support 10 or wall, and a camera 130 for obtaining an image of a specific body part of a patient may be installed at a part of the housing unit 112.

The subject check unit 120 is formed at a part of the housing unit 112, and disposed to overlap at least one surface of the subject whose position is aligned in the alignment area of the alignment unit 110 according to the alignment criteria.

The subject check unit 120 may be implemented with a transparent plate or transparent display, and installed in the housing unit 112 so as to surround a part of the alignment area. Thus, a patient or a specific body part of the patient positioned in the imaging area corresponding to the internal space of the housing unit 112 can be directly seen from outside.

For example, the subject check unit 120 may be formed of transparent glass or transparent synthetic rein. Desirably, the subject check unit 120 may be formed of an acrylic material. In this case, the subject check unit 120 simply projects and displays the patient or the specific body part of the patient positioned in the housing unit 112, that is, the imaging area beyond the subject check unit 120.

The subject check unit 120 may be configured to simply project only the figure of a patient. However, the subject check unit 120 may include a transparent display which displays various pieces of information for correcting the posture of the patient, while displaying a projected image of the patient or a specific body part of the patient.

For example, the subject check unit 120 displays the projected image of the patient or the specific body part of the patient and a guide line 121 overlapping the projected image, such that the operator can determine the posture of the patient. The guide line 121 may be formed in various shapes such that the operator can check and correct the posture of the patient. For example, the guide line 121 may include a vertical or horizontal line or a combination of vertical and horizontal lines crossing each other.

The guide line 121 is displayed to overlap a specific part of the subject in the subject check unit 120.

Thus, when a patient takes a posture and stands or sits in the housing unit 112, the operator determines the posture of the patient seen through the subject check unit 120 based on the guide line 121 displayed on the subject check unit 120, and checks and corrects the posture of the patient.

The guide line 121 may be formed by applying a specific color of paint, displayed as a plurality of pixels displayed on the screen of the subject check unit 120, or formed by irradiating a specific color of beam.

The guide line 121 according to the embodiment of the present invention may be formed by laser beam which is irradiated from the subject check unit 120.

When the subject check unit 120 is implemented with the transparent display, an image of the patient which is taken by the camera 130 may be displayed on the subject check unit 120 in real time, and the operator may compare the guide line 121 to the image of the patient and determine whether the posture of the patient is correct.

Furthermore, the image of the patient which is taken by the camera 130 may be displayed at a reference position of the subject check unit 120 in real time. Based on the displayed image, the operator can determine the patient or the specific body part of the patient projected on the subject check unit 120, and check and correct the posture of the patient.

The radiography machine may include a program which automatically compares the image displayed on the subject check unit 120 to the posture of the patient based on the guide line 121, such that the posture of the patient can be automatically checked.

The subject check unit 120 may be implemented with a transparent touch panel. In this case, the subject check unit 120 may be implemented with the transparent touch panel, or the transparent touch panel may be installed in a part of the subject check unit 120.

Through the transparent touch panel, the guide line 121 and the radiography settings may be selected, corrected or changed. At this time, the radiography machine may include a hardware device or program which receives an electrical signal outputted from the transparent touch panel and processes the received electrical signal as a user command for radiography.

When the subject check unit 120 is implemented with the transparent touch panel, the radiography machine may further include a preference setting interface (not illustrated) for controlling the detail settings of the radiography unit 111 according to an user command inputted to the touch panel.

The preference setting interface may be embedded in the housing unit 112 or electrically connected to the radiography unit 111 so as to control the detail settings. Through the preference setting interface, the operator who radiographs a patient can easily and conveniently control detail settings required for the radiography.

That is, the preference setting interface can minimize the moving line of the operator when the operator radiographs the patient. Through the preference setting interface, the operator can check the posture of the patient in a state where the operator stands in front of the patient, and control the settings of the radiography machine at a time.

In the above-described embodiment, when the subject check unit 120 includes a transparent display, the subject check unit 120 may display a projected image of a patient or a specific body part of the patient and various pieces of information for correcting the posture of the patient, such that the operator can directly correct the posture of the patient or the specific part of the patient based on the various pieces of information.

However, when the posture of the patient or the specific part of the patient displayed on the subject check unit 120 is corrected through the transparent touch panel so as to coincide with the various pieces of information displayed on the subject check unit 120, the radiography machine may be moved to set the patient or the specific part of the patient at the imaging area.

While various embodiments have been described above, it will be understood to those skilled in the art that the embodiments described are by way of example only. Accordingly, the disclosure described herein should not be limited based on the described embodiments.

INDUSTRIAL APPLICABILITY

The present invention can be used in a radiography machine for medical use, which is capable of radiographing a specific part of a patient.

The invention claimed is:

1. A radiography machine for radiographing a subject, comprising:
an alignment unit having an alignment area wherein the subject is disposed in the alignment area; and
wherein the alignment unit further includes:
a radiography unit including a radiation source and a detector;
a housing unit to house the radiation source and the detector, and defining the alignment area for the subject to be disposed between the radiation source and the detector, and the housing unit further including an opening; and
a transparent subject check unit installed in the opening of the housing unit to allow the subject to be visibly observed, wherein the transparent subject check unit displays guide lines, wherein the guide lines are arranged to form an overlay image on a specific body part of the subject as observed on the transparent subject check unit, and wherein the transparent subject check unit includes a touch panel, wherein the touch panel is used to select, correct, and change the guide lines.

2. The radiography machine of claim 1, wherein the housing unit is fixed to a support or a wall and is configured to be moved vertically.

3. The radiography machine of claim 1, wherein the housing unit includes a camera for obtaining an image of the subject.

4. The radiography machine of claim 3, wherein the image of the subject is displayed on the transparent subject check unit and compared with the guide lines in real time to determine a posture of the subject.

5. The radiography machine of claim 1, wherein the guide line is displayed on the transparent subject check unit by laser beam.

6. The radiography machine of claim 1, wherein a preference setting interface to control the radiography unit and embedded in the housing unit or electrically connected to the radiography unit.

* * * * *